US006417318B1

(12) United States Patent
Heydenreich et al.

(10) Patent No.: US 6,417,318 B1
(45) Date of Patent: Jul. 9, 2002

(54) PROCESS FOR THE REMOVAL OF DISSOLVED OXYGEN FROM PHENOL

(75) Inventors: Frieder Heydenreich, Düsseldorf; Rudolf Wagner, Köln, both of (DE); Michael Bödiger, League City, TX (US)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/777,152

(22) Filed: Feb. 5, 2001

(30) Foreign Application Priority Data

Feb. 10, 2000 (DE) .......................... 100 05 770

(51) Int. Cl.[7] .............................................. C08G 64/00
(52) U.S. Cl. ...................................... 528/196; 528/198
(58) Field of Search .................................. 528/196, 198

(56) References Cited

U.S. PATENT DOCUMENTS

| 2,597,492 A | 5/1952 | Hwa ........................... 210/24 |
| 2,597,493 A | 5/1952 | Hwa ............................ 260/47 |
| 2,616,877 A | 11/1952 | McMaster ................. 260/88.1 |
| 2,632,000 A | 3/1953 | McMaster et al. ......... 260/88.1 |
| 2,632,001 A | 3/1953 | McMaster et al. ......... 260/88.1 |
| 2,642,417 A | 6/1953 | Wheaton et al. ........... 260/88.1 |
| 2,960,480 A | 11/1960 | Thielen ....................... 260/2.1 |
| 2,992,544 A | 7/1961 | McMaster .................... 260/2.1 |
| 3,311,602 A | 3/1967 | Raley ......................... 260/93.5 |
| 3,437,699 A | 4/1969 | Flickinger .................... 260/621 |

FOREIGN PATENT DOCUMENTS

| CN | 1098384 | 2/1995 | |
| DE | 25 24 722 | 11/1976 | |
| GB | 867449 | 12/1958 | |
| JP | 58-79590 | 7/1983 | |
| JP | 6-3838 | 1/1994 | ............ G03G/5/05 |
| JP | 6-25398 | 2/1994 | ............ C08G/64/06 |
| JP | 6-49195 | 2/1994 | ............ C08G/64/04 |
| JP | 6-145317 | 5/1994 | ............ C08G/63/64 |
| JP | 6-216078 | 8/1994 | ......... H01L/21/302 |
| JP | 6-322094 | 11/1994 | ............ C08G/64/14 |
| JP | 8-134198 | 5/1996 | ............ C08G/64/06 |
| JP | 8-134199 | 5/1996 | ............ C08G/64/06 |

OTHER PUBLICATIONS

VGB Kraftwerkstechnik 64 (month unavailable), 1984, pp. 61–63, F. Martinola et al, "Ein Starkbasischer Anionenaustauscher Mit Zwei Funktionen".

*Primary Examiner*—Terressa M. Boykin
(74) *Attorney, Agent, or Firm*—Joseph C. Gil; Richard E.L. Henderson

(57) ABSTRACT

The present invention relates to a method for avoiding undesirable discoloration in polycarbonate production by catalytic removal of dissolved oxygen from phenol by (a) admixing hydrogen with phenol and
(b) passing the phenol stream over ion exchangers doped with platinum group metals.

12 Claims, No Drawings

PROCESS FOR THE REMOVAL OF DISSOLVED OXYGEN FROM PHENOL

BACKGROUND OF THE INVENTION

The invention relates to a process for the removal of dissolved oxygen from phenol by admixing water into the phenol, which is then passed over metals of the platinum group applied to supports in order to catalyze the reaction of hydrogen and oxygen to give water in accordance with the equation: $2H_2+O_2 \rightarrow 2H_2O$. The invention further relates to polycarbonate and bisphenol A that are prepared from oxygen-free phenol prepared by admixing water and subsequently passing the mixture over ion exchangers doped with platinum metal.

Phenol is an important unit in the preparation of the plastic polycarbonate. Phenol is first reacted with acetone under acid conditions to give bisphenol A. The molar ratio of the reactants phenol: acetone here is in the range of 8:1 to 14:1, preferably in the region of 12:1. Bisphenol A is then reacted with either phosgene or diphenyl carbonate to give polycarbonate in the following step.

This plastic is employed in a very wide-ranging spectrum of uses, inter alia in very demanding fields, such as in the preparation of high-quality optical materials and of compact discs and in the electronics field.

However, discoloration of the plastics often prevent their use in these applications, even when a very great effort is made to keep the quality of the starting substances at a high level.

It has now been found, surprisingly, that discoloration can be virtually completely avoided if hydrogen is added to the phenol and the mixture is then passed over a support, preferably an ion exchanger, doped with at least one metal of the platinum group.

How the discoloration arises has not yet been clarified in detail. At the moment, however, it is assumed that discoloration is caused by the nonselective action of oxygen present in the starting substances.

The invention relates to a process for the removal of dissolved oxygen from phenol by admixing hydrogen into the phenol, which is then passed over metals of the platinum group applied to supports in order to catalyze the reaction of hydrogen and oxygen to give water in accordance with the equation: $2H_2+O_2 \rightarrow 2H_2O$. The invention further relates to polycarbonate and bisphenol A that are prepared from oxygen-free phenol prepared by admixing hydrogen and subsequently passing the mixture over ion exchangers doped with platinum metal.

SUMMARY OF THE INVENTION

The present invention relates to a process for the catalytic removal of dissolved oxygen from phenol comprising
(a) admixing hydrogen with phenol and
(b) passing the phenol stream over ion exchangers doped with platinum group metals to catalyze the reaction $2H_2+O_2 \rightarrow 2H_2O$.

DETAILED DESCRIPTION OF THE INVENTION

The platinum metals to be used according to the invention are the elements of the series ruthenium, rhodium, palladium, osmium, iridium, and platinum. Palladium and platinum are preferred for the process according to the invention.

The ion exchangers to be used according to the invention are preferably anion exchangers and can contain weakly and/or strongly basic groups. Strongly basic exchangers in the Cl form or weakly basic anion exchangers in the free base form are particularly preferred. A crosslinked polymer of ethylenically unsaturated monomers is used as the base polymer. Examples of ethylenically monounsaturated monomers are, for example, styrene, vinyltoluene, ethylstyrene, α-methylstyrene, and derivatives thereof halogenated in the nucleus (such as chlorostyrene), vinylbenzyl chloride, acrylic acid and its salts and esters (particularly the methyl and ethyl esters), methacrylic acid and its salts and esters (particularly the methyl ester), and the nitriles and amides of acrylic and methacrylic acid.

The polymers are crosslinked, preferably by copolymerization with crosslinking monomers having more than one (preferably 2 or 3) copolymerizable C=C double bonds per molecule. Such crosslinking monomers include, for example, poly-functional vinylaromatics, such as di or trivinylbenzenes, divinylethylbenzene, divinyltoluene, divinylxylene, divinylethylbenzene, or divinylnaphthalene; poly-functional allylaromatics, such as di- or triallylbenzenes; polyfunctional vinyl or allyl-heterocyclic compounds, such as trivinyl or triallyl cyanurate or trivinyl or triallyl isocyanurate; $N,N'-C_1-C_6$ alkylenediacrylamides or dimethacrylamides, such as N,N'-methylenediacrylamide or -dimethacrylamide or N,N'-ethylenediacrylamide or -dimethacrylamide; polyvinyl or polyallyl ethers of saturated $C_2-C_{20}$–polyols having 2 to 4 OH groups per molecule, such as, for example, ethylene glycol divinyl or diallyl ether or diethylene glycol divinyl or diallyl ethers; esters of unsaturated $C_3-C_{12}$-alcohols or saturated $C_2-C_{20}$-polyols having 2 to 4 OH groups per molecule, such as allyl methacrylate, ethylene glycol di(meth)acrylate, glycerol tri (meth)acrylate, or pentaerythritol tetra(meth)acrylate; divinylethyleneurea, divinylpro-pyleneurea or divinyl adipate; or aliphatic or cycloaliphatic olefins having 2 or 3isolated C=C double bonds, such as hexa1,5-diene, 2,5-dimethylhexa1,5-diene, octa1,7-diene, or 1,2,4-trivinylcyclohexane. Divinylbenzene (as an isomer mixture) and mixtures of divinylbenzene and aliphatic $C_6-C_{12}$-hydrocarbons having 2 or 3 C=C double bonds have proved to be particularly suitable crosslinking monomers.

The crosslinking monomers are in general employed in amounts of 2 to 20% by weight, preferably 2 to 12% by weight, based on the total amount of polymerizable monomers employed.

The crosslinking monomers do not have to be employed in pure form but can also be employed in the form of their technical grade mixtures of lower purity (such as, for example, divinylbenzene mixed with ethylstyrene).

The crosslinked polymers can be further processed to give anion exchangers in a known manner. The anion exchangers can be prepared on the one hand by chloromethylation (cf. U.S. Pat. Nos. 2,642,417, 2,960,480, 2,597,492, 2,597,493, 3,311,602, and 2,616,877), preferably with chloromethyl ether, and subsequent amination (cf. U.S. Pat. Nos. 2,632,000, 2,616,877, 2,642,417, 2,632,001, and 2,992,544) with ammonia, a primary amine, such as methyl or ethylamine, a secondary amine, such as dimethylamine, or a tertiary amine, such as trimethylamine or dimethylisopropanolamine, at a temperature of as a rule 25 to 150° C.

On the other hand, the anion exchangers can be prepared by the aminomethylation process, in which (a) the crosslinked polymers are reacted with phthalimide derivatives and (b) the resulting imides are hydrated. The amidomethylation (a) can be carried out by reaction of the crosslinked polymers with N-chloromethyl-phthalimide in the presence of swelling agents for crosslinked polymers and Friedel-Crafts catalysts (DE-A 1,054,715), the phthalimide derivative being employed in amounts suitable for the desired level of substitution (0.3 to 2.0 substitutions per aromatic nucleus) of the aromatic nuclei present in the crosslinked polymer (or in an excess of up to 20%, preferably up to 10%).

Suitable swelling agents include halogenated hydrocarbons, preferably chlorinated $C_1$–$C_4$-hydrocarbons. The most preferred swelling agent is 1,2-dichloroethane.

Preferred Friedel-Crafts catalysts include, for example, $AlCl_3$, $BF_3$, $FeCl_3$, $ZnCl_2$, $TiCl_4$, $ZrCl_4$, SnC4, $H_3PO_4$, HF, and $HBF_4$. The catalysts can be employe amounts of 0.01 to 0.1 mol per mole of N-chloromethylphthalimide.

The reaction can be carried out, for example, by a procedure in which the crosslinked polymer is introduced into a solution of N-chloromethylphthalimide in a swelling agent and the reactants are allowed to act in the presence of the catalyst at elevated temperature, as a rule at 50 to 100° C., preferably 50 to 75° C., until the evolution of hydrogen chloride has substantially ended. This is in general the case after 2 to 20 hours. After separation of the substituted polymer and liquid reaction medium and inorganic products, it is advisable to take up the polymer in aqueous sodium chloride solution and to remove residues of swelling agent by distillation.

The hydrolysis (b) of the substituted polymer can be carried out, for example, by subsequently hydrolyzing the product that has been isolated with an approximately 5 to 40% strength by weight aqueous or alcoholic solution of an alkali, such as sodium hydroxide or potassium hydroxide, or with an approximately 5 to 50% strength by weight aqueous solution of a mineral acid, such as hydrochloric acid, hydrobromic acid, or sulfuric acid, in an autoclave at temperatures between 100 and 250° C. On the other hand, the intermediate product can also be reacted with a 5 to 50% strength by weight aqueous or alcoholic solution of hydrazine hydrate at temperatures of 50 to 100° C. In a preferred embodiment, the solution described last can contain other alkalis, in particular caustic alkalis, in amounts of 1 to 20% by weight. The reaction product can be isolated, washed with water and then heated with an aqueous solution of mineral acid (preferably 5 to 20% strength by weight) to bring the hydrolysis to completion.

The aminoalkyl compounds that can be obtained can be modified by alkylation. Known alkylating agents, such as, for example, methyl, ethyl, or propyl chlorides and bromides, dialkyl sulfates, alkylene oxides, halogenohydrins, polyhalogen compounds, epihalohydrins, and ethyleneimines, can be used for this purpose.

The above-mentioned alkylation of the said amino derivatives can be effected by reaction thereof with alkylating agents in molar amounts at temperatures of between 20 and 125° C. If, for example, alkyl halides or dialkyl sulfates are used, it is advisable to add the amount of an alkaline agent, such as sodium hydroxide, calcium carbonate, magnesium oxide, and the like, required for neutralization of the hydrogen halide acids or alkylsulfuric acids formed. Secondary, tertiary, or quaternary amino derivatives or mixtures thereof are obtained depending on the amount of alkylating agent used. A mixture of formaldehyde with formic acid is another customary alkylating agent which is used in the form of an aqueous solution, if appropriate in the presence of mineral acids. The reaction can be carried out with these alkylating agents at temperatures of between 50 and 120° C. In the latter case, tertiary amino derivatives are obtained as the sole reaction products if an excess of alkylating agent is used. The tertiary amino derivatives can be converted completely or partly into quaternary derivatives by carrying out a further reaction with alkylating agents, such as, for example, methyl chloride, at temperatures of between 10 and 120° C.

The anion exchangers used can be in gel form or, preferably, macroporous; those based on polystyrene are preferred. Strongly basic anion exchangers in the Cl form and weakly basic anion exchangers in the free base form are particularly preferred.

Doping of the anion exchangers with platinum metals, preferably platinum or palladium, can be carried out, for example, by a procedure in which the platinum metal, preferably platinum or palladium, in a suitable salt form is taken up by the groups with ion exchange activity and is then reduced, or reducing substances are first applied and the platinum metal, preferably platinum or palladium, is then precipitated on the resin from a suitable solution. Finally, colloidally dispersed platinum metal that has already been reduced, preferably platinum or palladium, can also be taken up adsorptively by the resin from a corresponding solution or suspension.

The application process which is particularly preferred in the present invention starts from the salt form of the resin, which is first treated with a palladium salt solution (for example, 2 to 20% strength by weight $Na_2PdCl_4$), the anion on the resin being exchanged for the anionic palladium complex. The palladium complex is chiefly distributed in the surface region of the resin grain, so that the regions which are distinguished by rapid kinetics are affected above all.

The reduction of the noble metal bonded ionogenically to the resin, for example, of palladium to metallic palladium, can be carried out by reducing agents that are usual for this type of reduction, such as hydrazine, hydroxylamine, hydrogen, ascorbic acid, formalin, or formic acid, in strongly alkaline solution at elevated temperature. Hydrazine or formalin is preferably used.

The noble metal content, preferably of platinum metal, of the ion exchangers to be used according to the invention is in general in the range from 0.3 to 10 g, preferably 0.5 to 1.2 g, per liter of anion exchanger.

DE-A 25 24 722 discloses the use of polystyrenes containing copper ions or cobalt ions for reduction of oxygen dissolved in water. U.S. Pat. No. 4,789,488 recommends palladium or platinum-doped anion exchangers for decreasing the oxygen content in aqueous systems with hydrogen. In addition to hydrogen, other reducing agents, such as, for example, hydrazine, have also already been described for removal of oxygen from water. Cf. F. Martinola et al., VGB Kraftwerkstechnik 64 (1984), pages 61–63. The use of metal-doped anion exchangers for simultaneous removal of oxygen and undesirable ions has also already been discussed. Cf. F. Martinola, loc. cit.

It has now been found that this process is very effective in avoiding discoloration in polycarbonate production by catalytic reduction of oxygen. The theory described above that the discoloration is to be attributed to traces of oxygen is thereby substantiated. Since phenol not only is the main component of the polyearbonate but is also present in a large excess in the preparation of bisphenol A and is at the start of the production sequence it is appropriate to use this process on this starting material.

EXAMPLE

Hydrogen at a rate of 50 to 100 l/hour was fed into a phenol stream having a 10 $m^3$/hour feed rate in a reactor for the preparation of bisphenol A. The temperature of the phenol was 50° C. to 80° C.

The system pressure of the bisphenol A production was in the range of 3–10 bar at an oxygen feed concentration of 0.1 mg/1 to 2 mg/1. The hydrogen-containing stream of phenol was passed through a reactor upstream of the bisphenol A production which was filled with a palladized weakly basic anion exchanger (0.5 m³ Lewatit® catalyst K3433, manufacturer Bayer AG).

The height of the resin was 0.5 mm, the specific load was 20 bed volumes/hour and the pressure loss was in the range of 0.08–0.2 bar.

The oxygen concentration measured in the discharge of the catalyst bed was only 0.01 to 0.03 mg/1.

In this procedure, the product discoloration index of the bisphenol A was 13 to 17 Hazen melt color index.

If the hydrogen feed was stopped and the stream of phenol and the catalyst were bypassed, the product discoloration index of the bisphenol A rose to >17 Hazen melt color index. The "Yellowness Index" of the polycarbonate changes accordingly from $\leq 1.7$ with phenol treated by the process according to the invention to $\geq 1.7$ without the treatment according to the invention.

What is claimed is:

1. A process for the catalytic removal of dissolved oxygen from phenol comprising
   (a) admixing hydrogen with phenol and
   (b) passing the phenol stream over an ion exchanger doped with a platinum group metal to catalyze the reaction $2H_2 + O_2 \rightarrow 2H_2O$.

2. A process according to claim 1 wherein the platinum group metal is an element selected from the group consisting of ruthenium, rhodium, palladium, osmium, iridium, and platinum.

3. A process according to claim 1 wherein the platinum group metal is platinum or palladium.

4. A process according to claim 1 wherein the ion exchanger is an anion exchanger with weakly and/or strongly basic groups.

5. A process according to claim 4 wherein the anion exchanger is a strongly basic anion exchanger in the C1 form or a weakly basic anion exchanger in the free base form.

6. A process according to claim 1 wherein the ion exchanger is a gel form or macroporous ion exchanger.

7. A process according to claim 1 wherein the ion exchanger contains 0.3 to 10 g of platinum metal per liter of ion exchanger.

8. A process for the preparation of oxygen-free phenol comprising adding hydrogen to the phenol and passing the resultant mixture over an ion exchanger doped with a platinum group metal.

9. A method for preparing bispenol A comprising reacting acetone under acidic conditions with phenol prepared by the process of claim 1.

10. A method for preparing a polycarbonate comprising reacting phosgene or diphenyl carbonate with bispenol A prepared by reacting acetone under acidic conditions with phenol prepared by the process of claim 1.

11. Bisphenol A prepared from oxygen-free phenol obtained by the process of claim 1.

12. A polycarbonate prepared from oxygen-free phenol obtained by the process of claim 1.

* * * * *